United States Patent [19]

Young

[11] Patent Number: 5,019,236

[45] Date of Patent: May 28, 1991

[54] RETRACTABLE MEMBER FOR FLUID, OPTICAL AND ELECTRICAL COMMUNICATION IN CAPILLARY ZONE ELECTROPHORESIS

[75] Inventor: James E. Young, La Honda, Calif.

[73] Assignee: Hewlett-Packard Company, Palo Alto, Calif.

[21] Appl. No.: 495,889

[22] Filed: Mar. 19, 1990

[51] Int. Cl.$^5$ .......................................... G01N 27/26
[52] U.S. Cl. ............................. 204/299 R; 204/180.1; 204/183.3; 204/300 R
[58] Field of Search ............ 204/180.1, 183.3, 299 R, 204/300 R

[56] References Cited

U.S. PATENT DOCUMENTS

| | | | |
|---|---|---|---|
| 4,515,676 | 5/1985 | Kawai et al. | 204/299 R |
| 4,705,616 | 10/1987 | Andresen et al. | 204/299 R |
| 4,816,123 | 3/1989 | Ogan et al. | 204/183.3 |
| 4,842,701 | 6/1989 | Smith et al. | 204/180.1 |
| 4,911,807 | 3/1990 | Burd | 204/183.3 |

Primary Examiner—John F. Niebling
Assistant Examiner—David G. Ryser

[57] ABSTRACT

An apparatus for operatively connecting an electrophoresis capillary tube to a housing assembly, wherein the connecting involves fluid, optical and electrical communication. A capillary cassette is removably fixed to the housing assembly and a detector door is pivoted into place to provide vacuum, electrical ground and optical detection of electrophoretic migration at an outlet end of the capillary tube. The vacuum connection is actuated by a cam mechanism which converts the pivoting motion of the detector door into a reciprocating motion of a vacuum connector which is selectively received within the capillary cassette. The cam mechanism includes an arcuate groove on the detector door, a fixed linear slot and a coupling of the vacuum connector, the arcuate groove and linear slot.

17 Claims, 7 Drawing Sheets

RETRACTABLE MEMBER FOR FLUID, OPTICAL AND ELECTRICAL COMMUNICATION IN CAPILLARY ZONE ELECTROPHORESIS

TECHNICAL FIELD

The present invention relates generally to electrophoretic processes and particularly to apparatus for performing capillary zone electrophoresis.

BACKGROUND ART

Applications for electrophoresis, an analytical technique for separating and identifying biologically important molecules in a sample, include the determination of a sample's homogeneity, the determination of molecular weights of proteins and nucleic acids, the mapping of nucleic acid primary structures, i.e. DNA and RNA sequence analyses, and the definition of phenotypic variance of a protein at the molecular level. Electrophoretic techniques rely on the fact that each molecular specie has a unique combination of mass, size, shape, charge, density and sub-unit structure, all of which result in mobility differences responsive to an electric field. Various electrophoretic techniques use one or more of these properties to cause varying degrees of molecular separation via the migration of the molecular species under a constant or varying electric field.

Capillary zone electrophoresis is a technique using a capillary tube which is filled with a conductive fluid, or buffer solution. A small amount of a sample is introduced at one end of the capillary tube, whereafter a high potential difference is applied across the ends of the tube. Differences in the electrophoretic mobilities of different molecules cause the constituents of the sample to emerge separated at the outlet end of the capillary tube. Capillary zone electrophoresis is described in detail in U.S. Pat. No. 4,842,701 to Smith et al.

Typically, the capillary tube is encased within a linear housing, as shown in U.S. Pat. No. 4,705,616 to Andresen et al. Access to the capillary tube through the encasement is difficult, at best. Yet, access is desirable since capillary tubes have a tendency to clog. A clogged capillary tube normally is not repairable and, therefore, must be replaced.

In addition to the need to periodically repair or replace a clogged capillary tube, free access to the tube is desirable because it permits a change of capillary tubes to best fit an application. As noted above, there are a great number of applications for capillary zone electrophoresis. Operational characteristics vary with the application. Large diameter electrophoresis capillary tubes permit a greater current flow, but the increased current and the greater susceptibility to convection heating translates into a greater concern for the effects of heating than must be faced in use with small diameter capillary tubes. Heat affects, and may even destroy, the quantitative and qualitative analysis. On the other hand, use of a small diameter capillary tube makes detection of sample constituents more difficult. As the separated molecular constituents of a sample migrate toward the outlet end of the capillary tube, an electropherogram is obtained by employment of an optical detector. Optimally, the electropherogram shows spaced-apart peaks for the individual constituents of the sample. Small diameter capillary tubes are less conducive to such detection. Thus, the operational characteristics of a particular application are a factor in determining the preferred capillary tube diameter for that application. Likewise, the operational characteristics must be considered in any decision as to the length of the capillary tube for a particular application.

A problem with accommodating free replacement of capillary tubes, however, involves designing an electrophoretic apparatus which permits the user to efficiently connect and disconnect the many operational attachments needed for capillary zone electrophoresis. Proper operation requires fluid, optical and electric communication between the capillary tube and outside sources and detectors. For example, the capillary tube must intersect the optical axis of a detector beam source, with a sensor disposed in alignment for monitoring electrophoretic migration occurring within the capillary tube. Additionally, one end of the capillary tube must be received within a vial containing the sample connected to a power source. The opposite end must be received in a buffer vial in communication with the power source to provide a high potential difference across the capillary tube. Another attachment is to a source of vacuum which allows vacuum injection of the sample into the capillary tube. Moreover, a cooling medium may be brought into contact with the exterior of the capillary tube to dissipate heat produced by the electrophoretic process.

It is an object of the present invention to provide an electrophoretic separation apparatus in which a user may quickly and efficiently make those attachments necessary to affect capillary zone electrophoresis.

DISCLOSURE OF THE INVENTION

The above object has been met by an electrophoretic apparatus having a housing assembly, a capillary cassette and a door member which is displaced to selectively provide fluid, optical and electrical communication between the housing assembly and the capillary cassette. The door member is hinged to the housing assembly to pivot between an open position spaced-apart from the capillary cassette and a closed position which aligns optical detection, vacuum injection and electrical connections for electrophoretic analysis. A cam mechanism converts the pivoting movement of the door member into linear movement of a vacuum connector to insure the proper seal of the connection upon insertion of the connector into the capillary cassette.

The housing assembly includes the power source, a vacuum source and a detection beam source. A capillary tube is removably fixed within the cassette and has opposite ends inserted into a sample vial and a buffer vial. A fastening device secures the cassette to the housing assembly.

The detector door contains a photodiode or an array of photodiodes in alignment for sensing the optical beam which originates from the housing assembly and intersects the capillary tube within the capillary cassette. A signal is generated having a characteristic corresponding to beam intensity. Since molecules migrating through the capillary tube affect beam intensity, detection of fluctuating beam intensity provides electrophoretic analysis.

In addition to moving a detection device into and out of alignment with an optical axis, pivoting of the detector door causes linear reciprocation of a vacuum connector. The vacuum connector is slidably received into fluid communication with the capillary cassette upon closing of the detector door. Converting the pivoting motion of the detector door into linear motion of the vacuum connector is brought about by coupling the vacuum connector to a linear slot in the housing assembly and an arcuate groove in the detector door. As the door is pivoted, a pin extending from the vacuum connector is caused to travel along the arcuate groove, but the linear slot in the housing assembly confines the vacuum connector to reciprocating linear movement.

An advantage of the present invention is that the capillary cassette can be quickly and easily attached and detached from the housing assembly for replacement of capillary tubes. Pivoting of the detector door into the closed position provides fluid and optical communication between the components. Moreover, preferably the detector door includes an electrical contact which provides the ground contact to one end of the capillary tube, so that the detector door also provides electrical communication among the components.

BEST MODE FOR CARRYING OUT THE INVENTION

Figure 1:
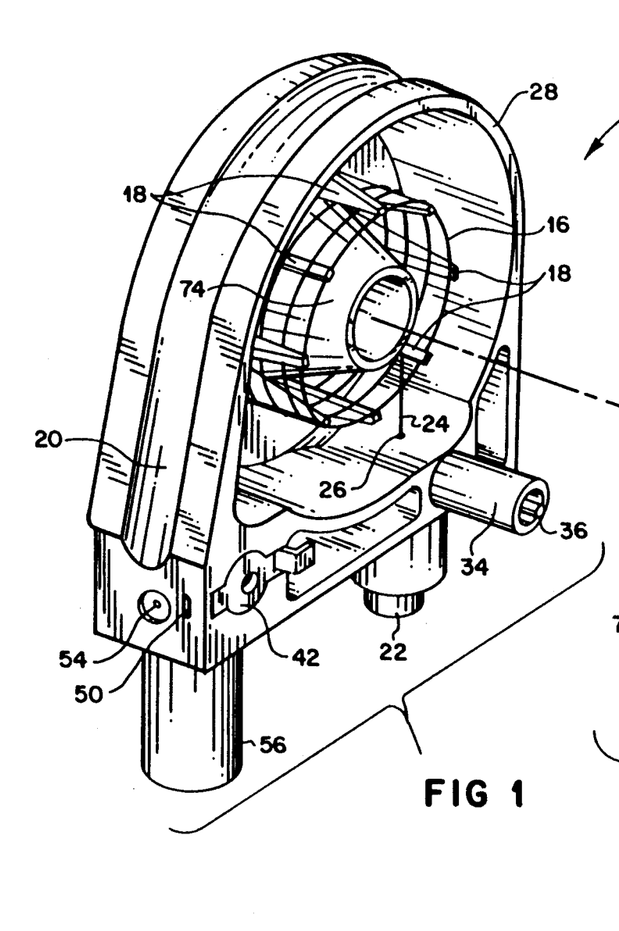
FIG. 1 is a perspective view of a capillary cassette for supporting a capillary tube for attachment to a support structure.
Figure 2:
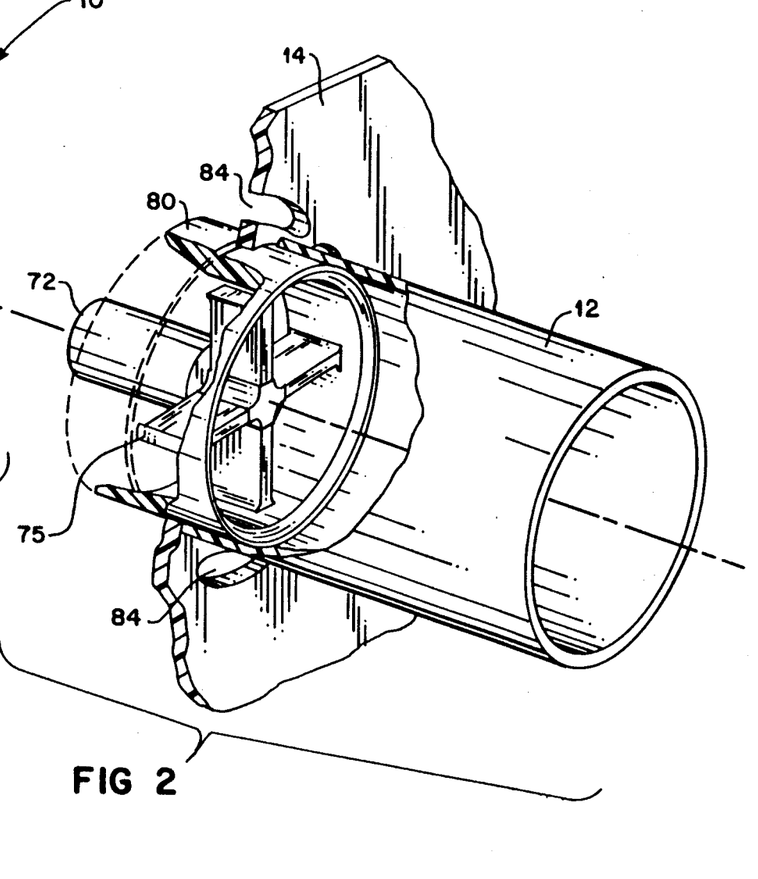
FIG. 2 is a perspective view of a support structure for the capillary cassette of FIG. 1.

With reference to FIGS. 1 and 2, a capillary cassette 10 is shown in alignment for attachment to a fixed support structure which includes a cylindrical fan housing 12 and a front support wall 14. A capillary tube 16 is maintained in a coiled condition by a capillary basket that includes a series of ribs 18 that alternate in orientation. The capillary cassette 10 is removably attached to the front support wall 14. A groove 20 about the exterior of the capillary cassette facilitates gripping of the member during removal.

Figure 3:
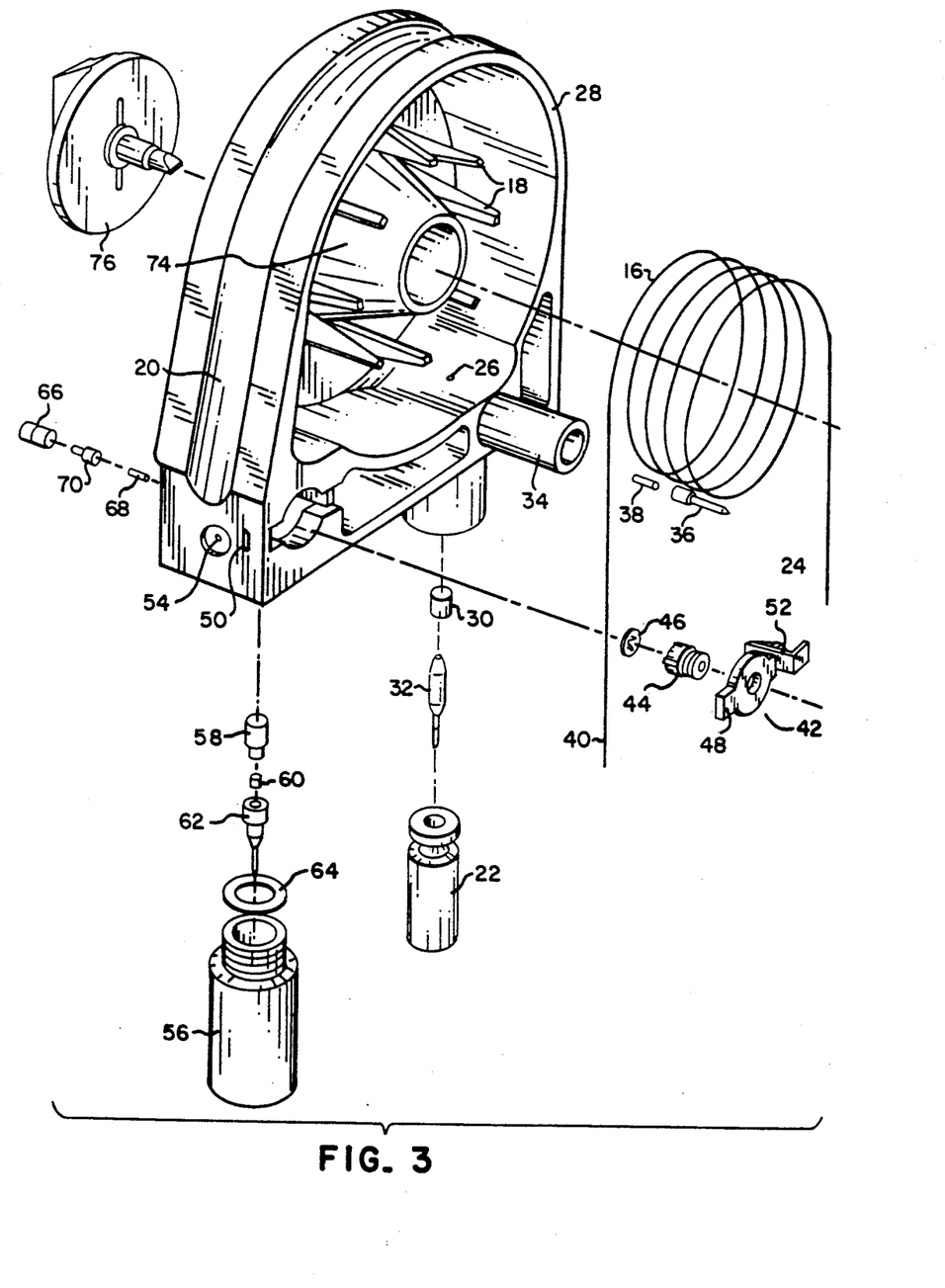
FIG. 3 is an exploded view of the capillary cassette of FIG. 1.

In capillary zone electrophoresis, separation of molecules occurs within the capillary tube 26. Referring to FIGS. 1 and 3, a sample vial 22 is attached at an inlet end 24 of the capillary tube 16. The inlet end 24 is inserted into a small diameter bore 26 in a cassette shell 28, then passes through an anode insert 30 for attachment to an anode electrode 32. The capillary tube 16 is filled with a conductive fluid, or buffer, after which a small amount of the sample to be separated is introduced at the inlet end 24 either hydrodynamically or electroosmotically. A d.c. potential of up to 30,000 volts is applied at the anode electrode 32 to provide an electromotive force for separation of molecules. The separation is a result of differences in electrophoretic mobility of the molecules.

A protective sleeve 34 projecting from the cassette shell 28 encases an anode contact 36 and a helical spring 38. The helical spring is metallic and is included to ensure electrical communication between the anode contact 36 and the anode insert 30. Upon mounting of the capillary cassette 10 onto the support structure identified above, the protective sleeve 34 is slidably received within the support wall of the structure and the anode contact 36 is caused to make contact with a source of power.

The construction of the capillary tube 16 is known in the art. Preferably, for the present invention the capillary tube is made of fused-silica. A fused-silica tube may be trained into the illustrated helical condition by the ribs 18 of the capillary basket, but such a tube is characterized by a memory which urges return of the capillary tube into a generally straight condition. Typically, the capillary tube has an inside diameter of 50 micron and outside diameter of 375 micron, but these dimensions are not critical. The ribs 18 of the capillary basket accommodate 20 cm to 1 meter long fused-silica capillary tubes. Often the fused-silica is encased within a coating of polyimide. Alternatively, the capillary tube may be a rigid member, manufactured to remain in a fixed, wound condition.

The embodiment, the polyimide coated, fused-silica capillary tube 16 is cut to a desired length and the inlet end 24 of the capillary tube is brought into fluid communication with the sample vial 22 and into electrical communication with a source of high voltage via the anode contact 36. Approximately 3 cm from an outlet end 40 of the capillary tube 16, a window is formed through the polyimide coating. The outlet end 40 is inserted into the capillary shell 28 and the window is aligned along an optical path provided by an aperture clip 42, an aperture mount having a helical spring 44 and an optical aperture member 46. The combination of the aperture mount and the optical aperture member secures the capillary tube in the desired position. The aperture clip 42 is a snap-in member which allows a user to quickly align and clamp the capillary tube without the use of tools. A projecting end 48 of the aperture clip 42 is received within a seat 50 in the cassette shell 28. The opposite end 52 of the aperture clip is selectively released from the cassette shell by a slight bending action of the member. Each of the members 42, 44 and 46 which seat the outlet end 40 of the capillary tube allows passage of optical detection such as by an ultraviolet absorbance detector.

Adjacent to the seat 50, which receives the projecting end 48 of the aperture clip 42, is a vacuum port 54 which is used in drawing a sample from the sample vial 22. The outlet end 40 of the capillary tube 16 is in fluid communication with a reservoir vial 56. To properly mount the outlet end with the reservoir vial, the capillary tube progresses through a cathode insert 58, a deformable ferrule 60, a cathode electrode 62 and a vacuum seal 64. The cathode electrode 62 is an electrical communication with a cathode connector 66 that is received within a bore, not shown, in the front of the cassette shell 28. A cathode spring 68 biases a plunger 70 and the cathode connector 66 into contact with a member at ground potential relative to the positive potential at the inlet end 24 of the capillary tube.

Referring now to FIGS. 1-3, in attaching the capillary cassette 10 to the support structure which includes the cylindrical fan housing 12 in the front support wall 14, a seating rod 72 of the support structure is received within a frustroconically shaped wall 74 of the capillary cassette. Four radial arms 75 secure the seating rod 72. A locking knob 76, shown in FIG. 3, is inserted into the seating rod of the support structure, whereafter a 90° turn of the locking knob causes fastening of the capillary cassette 10 to the support structure. In connecting the capillary cassette to the support structure, the window in the capillary tube is aligned for optical viewing by an ultraviolet absorbance detector, the anode contact 36 is brought into electrical connection with a source of 30,000 volts, and the capillary tube is positioned to receive a cooling flow of pressurized air generated by a rotary fan, not shown.

As best seen in FIG. 2, the cylindrical fan housing 12 has a projecting wall 80 which extends into the capillary cassette to encircle the capillary tube. The rotary fan generates a stream of pressurized air which enters the capillary region defined between the projecting wall 80 and the frustroconically shaped wall 74. The gas stream is a transverse flow relative to the capillary tube. That is, the major directional component of the gas flow through the capillary region is perpendicular to the molecular flow through the capillary tube. The stream of gas then follows the wall of the cassette shell 28 for return to the interior of the support structure via crescent-shaped openings 84 in the front support wall 14.

Figure 4:
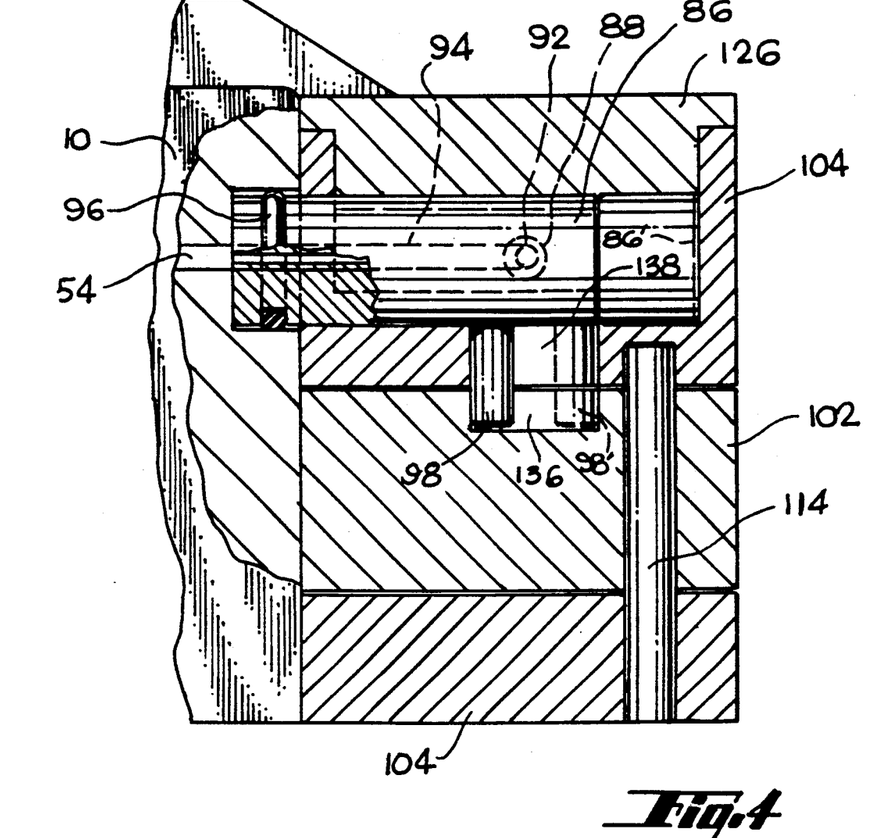
FIG. 4 is a side sectional view of a vacuum connector and cam mechanism for linearly driving the vacuum connector in accord with the present invention.
Figure 4A:
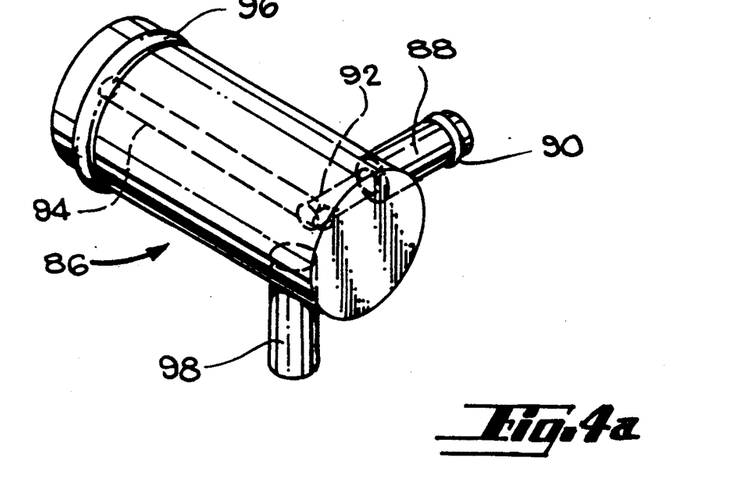
FIG. 4a is a perspective view of the vacuum connector of FIG. 1.

As noted above, the vacuum port 54 of the capillary cassette 10 is used in drawing a sample from the sample vial 22 into the capillary tube 16. FIGS. 4 and 4a illustrate a vacuum connector 86 for selectively evacuating air from the vacuum port 54 of the cassette 10. The vacuum connector is a cylindrical member having a projecting outlet 88 for attachment to a hose, not shown. An expanded region 90 of the outlet 88 accommodate a snug fit of the hose to the outlet. A pair of passageways 92 and 94 permit fluid communication between the outlet 88 and the vacuum port 54 of the cassette 10. An o-ring 96 at the end of the cylindrical connector 86 is used as a seal to prevent escape of pressure.

Extending downwardly from the vacuum connector 86 is a pin 98 which is employed to cause the vacuum connector to linearly retract from the cassette 10 to the position indicated by phantom lines 86' and 98' in FIG. 4. The camming mechanism for the linear reciprocation of the vacuum connector 86 is best seen with reference to FIGS. 7 and 8. The electrophoresis apparatus includes the support structure, or housing assembly 100, the capillary cassette 10 and the detector door 102. The housing assembly 100 has a projecting portion 104 which abuts the lateral side of the capillary cassette 10. This projecting portion 104 secures a hinge pin, not shown, for pivoting of the detector door 102 from the closed position of FIG. 7 to the open position of FIG. 8. Pivoting of the detector door provides fluid communication between the housing assembly and the capillary cassette, and provides optical and electrical communication among the housing assembly, the capillary cassette and the detector door.

Optical communication among the members 10, 100 and 102 permits monitoring of electrophoretic migration within the capillary tube of the cassette 10. A beam source within the housing assembly defines an optical path which intersects the capillary tube via the aperture clip 42, the aperture mount 44 and the optical aperture member 46 shown in FIG. 3. Approximately 3 cm from the outlet end 40 of the capillary tube 16, a window is formed through the polyimide coating of the tube. Migration of molecules past the window of the capillary tube affects the intensity of the beam which passes through the tube. Returning to FIG. 7, a photodiode detector 106 is aligned to monitor beam intensity exiting from the capillary cassette 10. The photodiode detector generates a signal having a characteristic corresponding to beam intensity. This signal is forwarded to the housing assembly for obtaining a quantitative and qualitative analysis of the electrophoretic migration. Both the housing assembly and the detector door include frustoconically shaped protrusions 108 and 110 which are received within the capillary cassette to prevent entrance of ambient light.

Electrical communication among the members 10, 100 and 102 is provided by a contact on the forward face 112 of the detector door 102. The contact on the front face is at ground potential of the high voltage power source in the housing assembly 100. Closing of the detector door brings the contact into abutting relation with the cathode connector 66, shown in FIG. 3, on the capillary cassette. In this manner, the outlet end 40 of the capillary tube 16 is placed at ground potential.

Figure 5:
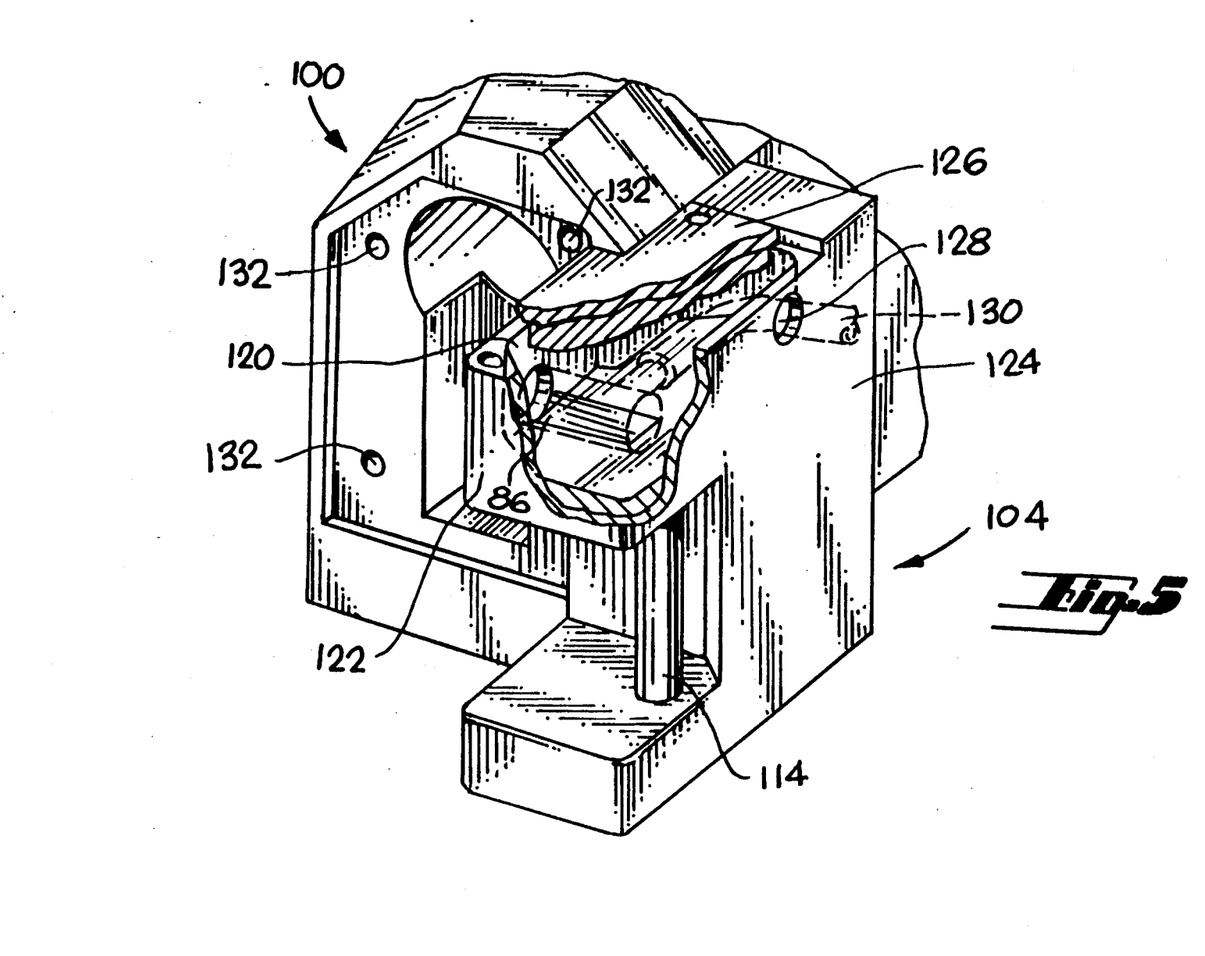
FIG. 5 is a perspective view of a portion of the support structure of FIG. 2.
Figure 6:
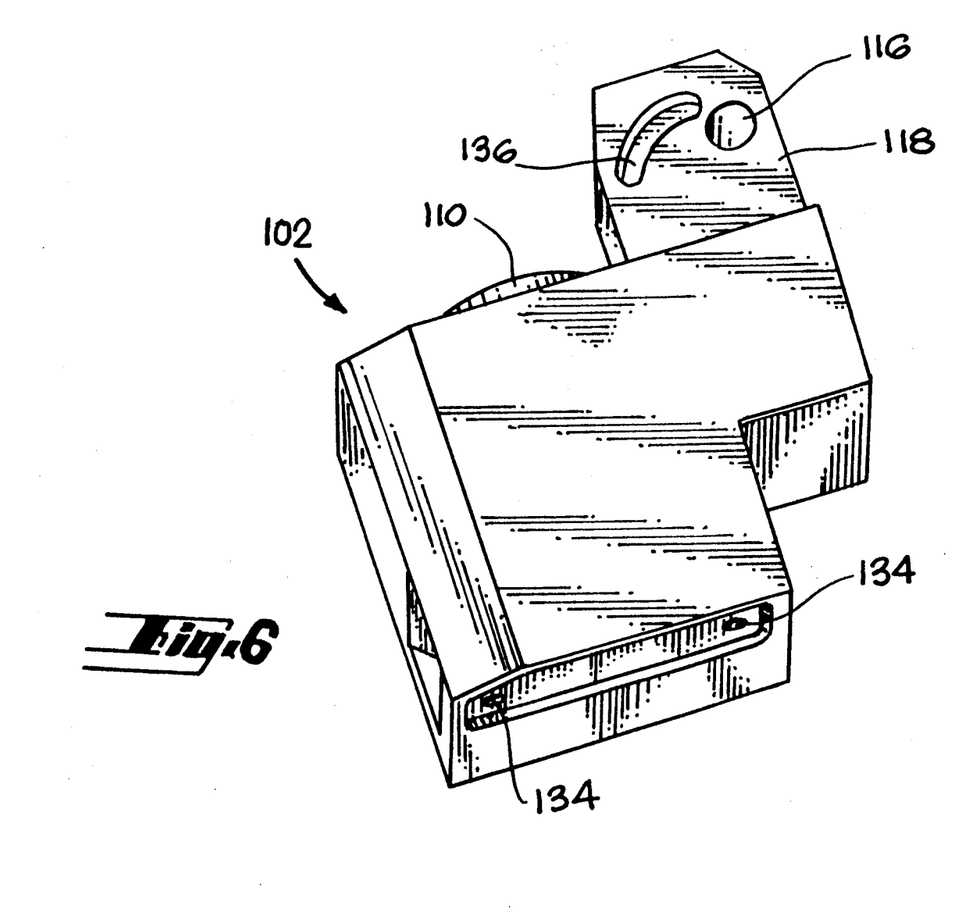
FIG. 6 is a top perspective view of the detector door of FIG. 4.

Fluid communication between the capillary cassette 10 and the housing assembly 100 is likewise initiated by displacement of the detector door 102 from the open position to the closed position. The projecting portion 104 of the housing assembly 100 is shown in detail in FIG. 5, while the detector door is shown in FIG. 6. A hinge pin 114 is received within the c-shaped portion of the housing assembly, and when fully assembled penetrates a bore 116 within the hinged portion 118 of the detector door 102. The detector door pivots about an axis defined by the hinge pin 114.

The upper region of the c-shaped portion 104 has a chamber defined by walls 120, 122 and 124 and a cover 126. An aperture 128 within the wall 124 receives a hose 130 for attachment to the vacuum connector 86. The hose 130 is made of a flexible material so as not to hinder the linear reciprocating motion of the vacuum connector. The end of the hose opposite the vacuum connector is attached to a vacuum source which is typically contained within the housing assembly 110. However, the source of vacuum pressure may be outside of the housing assembly.

FIG. 5 illustrates that portion of the housing assembly 100 dedicated to projection of the detector beam for monitoring electrophoretic migration within the capillary cassette. The front plate is not shown, but is attached to the housing assembly by means of bolts which are threaded into holes 132. The detector door 102 of FIG. 6 is likewise missing a surface plate which attaches to internally-threaded holes 134 during installation of the detector or detector array within the door member.

The hinged portion 118 of the detector door 102 includes an arcuate groove 136. The arcuate groove initiates motion of the vacuum connector 86 upon pivoting of the detector door. Referring again to FIGS. 4 and 4a, the downwardly depending pin 98 of the vacuum connector 86 penetrates a linear slot 138 in the c-shaped portion 104 of the housing assembly and has an end extending into the arcuate groove 136 of the detector door 102. Pivoting of the door causes the end of the pin 98 to follow the contour of the arcuate groove 136, but the linear slot 138 confines the pin and the vacuum connector 86 to linear movement. This camming mechanism is best described by reference to the positions of FIGS. 7 and 8.

Figure 7:
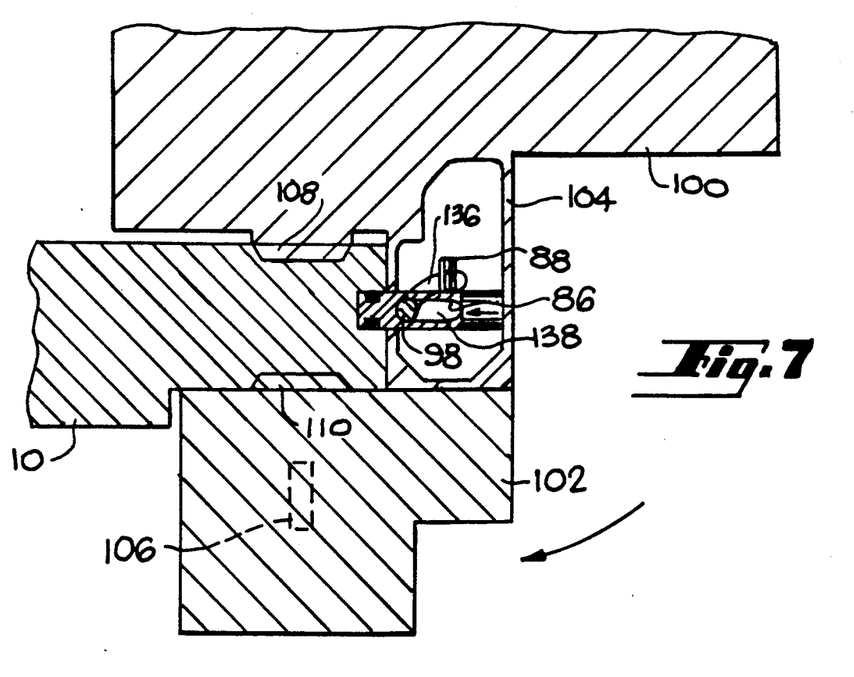
FIG. 7 is a top sectional view of the detector door FIG. 6 shown in a closed position.

In the closed position of FIG. 7, the pin 98 of the vacuum connector 86 is at forward ends of both the linear slot 138 and the arcuate groove 136. In this position, the vacuum connector 86 is in a forward, engaged position with the capillary cassette 10. That is, the vacuum connector is in fluid communication with the capillary cassette. The arcuate groove 136 is displaced in response to pivoting of the detector door 102 into the open position shown in FIG. 8. Displacement of the arcuate groove 136 causes the pin 98 to follow the contour of the arcuate groove, and in doing so the pin is moved to the rearward end of the linear slot 138. In this manner, the vacuum connector 86 is disengaged from the capillary cassette 10. Return of the detector door 102 to its closed position returns the vacuum connector to an engaged position.

Figure 8:
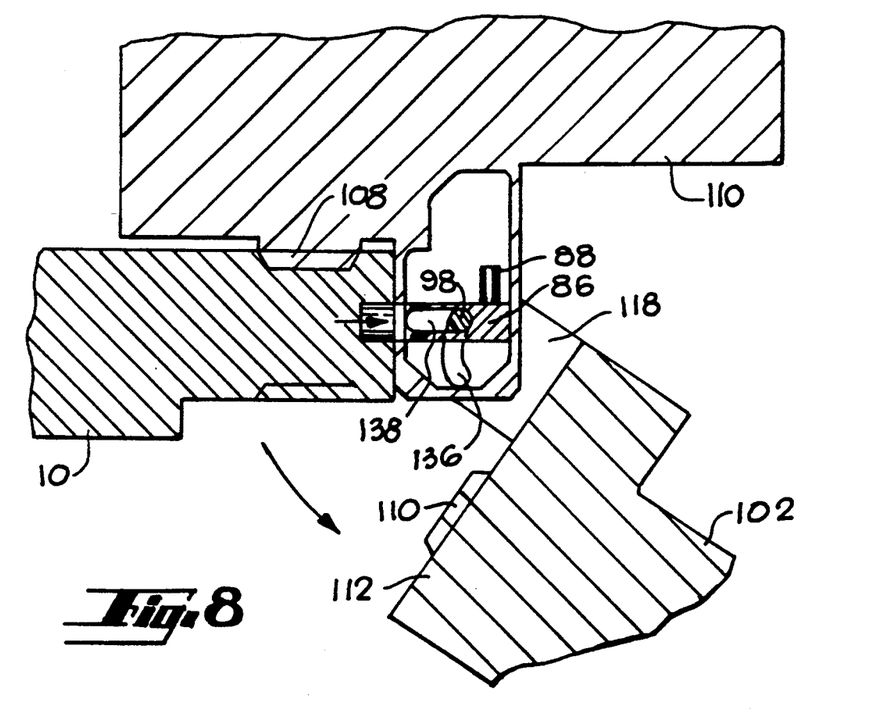
FIG. 8 is a top sectional view of the detector door of FIG. 6 shown in an open position.

Thus, the camming action of the detector door arcuate groove 136, the housing assembly linear slot 138 and the downwardly depending pin 98 of the vacuum connector 86 converts the pivoting motion of the detector door 102 into a linear reciprocating motion of the vacuum connector.

Referring to the drawings in general, an advantage of the present invention is that the capillary tube 16 can be readily replaced to suit the application. Reinstating the capillary tube into an operational condition requires only two motions. Firstly, the capillary cassette 10 is locked to the housing assembly 100 by a quarter-turn locking knob 76, shown in FIG. 3. This aligns the outlet end 40 of the capillary tube within the optical path defined by the housing assembly and directed through the aperture clip 42, the aperture mount 44 and the optical member 46. Fastening of the capillary cassette also provides the high-voltage potential at the inlet end 24 of the capillary tube, via the anode contact 36. Moreover, the capillary tube is in position to receive a cooling flow of air directed from a fan in the housing assembly.

The second motion which brings the capillary tube 16 into an operational condition is the pivot of the detector door 102 from an open position to a closed position. In a closed position, the outlet end 40 of the capillary tube is brought to a ground state by contact of the front face 112 of the detector door with a cathode connector 66 on the capillary cassette. Additionally, the detector 106, or detector array, is brought into alignment for monitoring beam intensity along the optical path after striking the capillary tube. Beam intensity permits the quantitative and qualitative analysis of electrophoretic migration. Lastly, detector door pivot is converted into a linear motion of the vacuum connector 86. When the detector door is in the closed position, communication of vacuum pressure through the connector is experienced at the outlet end 40 of the capillary tube. The vacuum pressure is used to draw the sample from the sample vial 22 for the electrophoretic process.

I claim:

1. An apparatus for operatively connecting an electrophoresis capillary tube to a housing assembly for fluid, optical and electrical communication between said capillary tube and said housing assembly, said apparatus comprising, a capillary cassette having mounting means for removably attaching said cassette to said housing assembly, said cassette having a capillary tube secured therein, a door member having hinge means for pivotally connecting said door means to said housing assembly, said door member having an open position in spaced relation to said cassette and having a closed position in contact with said cassette, detector means fixed to said door member for monitoring electrophoretic migration, said detector means being in alignment to optically monitor said migration within said capillary tube when said detector door is in said closed position, and vacuum means for selectively channeling a vacuum pressure to said capillary tube, said vacuum means having a fitting coupled to said door member in a manner to cause displacement of said fitting in response to said pivoting door member, said fitting being disposed to provide fluid communication with said capillary cassette when said door member is in a closed position.

2. The apparatus of claim 1 wherein said fitting of said vacuum means is coupled to said door member by a cam means for linearly displacing said fitting in response to said pivoting of said door member.

3. The apparatus of claim 2 wherein said cam means includes a fixed linear pathway and includes an arcuate pathway in said door member for displacement therewith, and further includes a means linking said fitting to said pathways for converting pivot of said door member to linear reciprocation of said fitting.

4. The apparatus of claim 3 wherein said means for converting door pivot to linear reciprocation of said fitting includes a pin extending from said fitting and received in each of said pathways, said linear pathway confining said fitting to a motion corresponding to said linear pathway.

5. The apparatus of claim 1 wherein said closed position of the door member aligns said detector means in an optical path defined by a beam source within said housing assembly to sense light directed through said capillary tube from said beam source.

6. The apparatus of claim 1 wherein said door member includes means for establishing electrical communication between said cassette and said housing assembly to cause electrophoretic migration, said means for establishing electrical communication being electrically isolated from said cassette when said door member is in said open position.

7. An apparatus for providing operative attachments between a housing assembly and electrophoresis device comprising, a door member pivotally attached to said housing assembly, said door member having a closed position in engagement with said electrophoresis device and having an open position, detector means coupled to said door member for monitoring electrophoretic migration occurring within said electrophoresis device, said detector means having an alignment to optically monitor said electrophoretic migration when said door member is in said closed position, a linearly reciprocating vacuum member supported in said housing assembly, said vacuum member having a retracted position spaced apart from said electrophoresis device and having an engaged position in which a passageway of said vacuum member is in vacuum-transfer engagement with said electrophoresis device, and means for converting pivoting motion of said door member into linear motion of said vacuum member, said vacuum member being displaced from said retracted position toward said engaged position as said door member is pivoted toward said close position.

8. The apparatus of claim 7 wherein said motion converting means is a cam assembly.

9. The apparatus of claim 8 wherein said cam assembly includes a linear pathway in said housing assembly and an arcuate pathway in said door member, said vacuum member being coupled to each of said pathways, said linear pathway confining said vacuum member to reciprocating linear motion relative to said electrophoresis device.

10. The apparatus of claim 9 wherein said vacuum member includes a pin extending into each of said pathways.

11. The apparatus of claim 7 further comprising contact means for establishing electrical communication between said housing assembly and said electrophoresis device, said contact means having a conductive member fixed to said door member, said conductive member being spaced apart from said electrophoresis device when said door member is in said open position.

12. The apparatus of claim 7 wherein said detector means includes a photodiode fixed to said door member.

13. The apparatus of claim 7 wherein said vacuum member is a connector having a portion slidably received in said electrophoresis device when said door member is in said closed position.

14. An electrophoresis device comprising,
a housing assembly having a power supply, a vacuum source and a detector beam source,
a capillary cassette removably fixed to said housing assembly, said capillary cassette having a capillary tube intersecting the optical axis defined by said detector beam source,
slidable means for selectively channeling vacuum pressure from said vacuum source to said capillary cassette,
a detector door pivotally attached to said housing assembly, said detector door having a closed position in engagement with said capillary cassette and having an open position, said detector door having a detector means in alignment with said optical axis when said detector door is in said closed position, said detector door further having means for establishing electrical communication between said power source and said capillary cassette, and
cam means coupling said detector door and said slidable means for linearly driving said slidable means in response to pivoting motion of said detector door, said cam means driving said slidable means into fluid communication with said capillary cassette upon movement of said detector door into said closed position.

15. The device of claim 14 wherein said cam means includes a fixed linear slot in said housing assembly and an arcuate groove in said detector door, said slidable means being coupled to said linear slot and said arcuate groove such that pivoting of said detector door causes relative motion between said slidable means and each of said linear slot and arcuate groove to linearly displace said slidable means.

16. The device of claim 15 wherein said slidable means is a connector having a pin extending therefrom, said pin being received in said linear slot and said arcuate groove.

17. The detector door of claim 14 wherein said detector means includes a photodiode.

* * * * *